United States Patent
Sakamoto et al.

(10) Patent No.: US 7,166,452 B2
(45) Date of Patent: Jan. 23, 2007

(54) AMINOKETONE ASYMMETRIC REDUCTASE AND NUCLEIC ACID THEREOF

(75) Inventors: Keiji Sakamoto, Takaoka (JP); Shinji Kita, Takaoka (JP); Kazuya Tsuzaki, Takaoka (JP); Tadanori Morikawa, Takaoka (JP); Sakayu Shimizu, Kyoto (JP); Michihiko Kataoka, Kyoto (JP)

(73) Assignee: Daiichi Fine Chemical Co., Ltd., Toyama (JP)

( * ) Notice: Subject to any disclaimer, the term of this patent is extended or adjusted under 35 U.S.C. 154(b) by 398 days.

(21) Appl. No.: 10/469,682

(22) PCT Filed: Mar. 1, 2002

(86) PCT No.: PCT/JP02/01928

§ 371 (c)(1),
(2), (4) Date: Sep. 2, 2003

(87) PCT Pub. No.: WO02/070714

PCT Pub. Date: Sep. 12, 2002

(65) Prior Publication Data

US 2004/0247583 A1  Dec. 9, 2004

(30) Foreign Application Priority Data

Mar. 2, 2001 (JP) .............................. 2001-058698

(51) Int. Cl.
- C12N 9/02 (2006.01)
- C12P 13/00 (2006.01)
- C12P 1/06 (2006.01)
- C12P 1/04 (2006.01)

(52) U.S. Cl. ...................... 435/189; 435/128; 435/169; 435/170

(58) Field of Classification Search .................. None
See application file for complete search history.

(56) References Cited

U.S. PATENT DOCUMENTS 4,237,304 A  12/1980  Dowd et al. ................. 548/239

FOREIGN PATENT DOCUMENTS

| EP | 0 654 534 A2 | 5/1995 |
|---|---|---|
| JP | 60-172953 | 9/1985 |
| JP | 8-98697 | 4/1996 |
| JP | 9-241231 | 9/1997 |
| WO | WO 01/73100 A1 | 10/2001 |

OTHER PUBLICATIONS

Morell et al. J. Lipid Res. 1972, 13, 293-310.*

Pascale Besse, et al. "Enantioselective Synthesis of Both Enantiomers of Cathinone via the Microbiological Reductions of 2-Azido-1-phenyl-1-propanone" J. Org. Chem. 1994, vol. 59, pp. 8288-8291.

John A. Hill, et al., "Enantiospecific Synthesis of [1-3H]-(+)-Pseudoephedrine Hydrochloride", Journal of Labelled Compounds and Radiopharmaceuticals, vol. 28, No. 6, 1990, pp. 681-689.

International Search Report dated Jun. 4, 2002, 2 pages.

Patent Abstracts of Japan, Publication No. 60-172953, dated Sep. 6, 1985, 1 page.

Patent Abstracts of Japan, Publication No. 09-241231, dated Sep. 16, 1997, 1 page.

Hermann Pfanz, et al., "Phenylmethylaminopropanol", Ger. (East) 13,683, Aug. 27, 1957, 3 pages as referenced in Pharmaccuticals, Cosmetics, Perfumes, vol. 53 (1959).

English Translation of the International Preliminary Examination Report issued for PCT application No. PCT/JP02/01928 filed on Mar. 1, 2002. (4 pages).

* cited by examiner

*Primary Examiner*—Rebecca E. Prouty
*Assistant Examiner*—Md Y. Meah
(74) *Attorney, Agent, or Firm*—Osha Liang L.L.P.

(57) ABSTRACT

A protein, which is an aminoketone asymmetric reductase, having an effect of producing d-pseudoephedrine by acting on 1-2-methylaminopropiophenone, and having the following physiochemical properties:

- substrate: 1-2-methylaminopropiophenone
- optimum pH: pH 8.1
- optimum temperature: 55° C.
- coenzyme: NADP
- molecular weight: about 28500 Da homotetramer and a nucleic acid coding the protein.

4 Claims, 2 Drawing Sheets

SUBUNIT Mr 28.5kda 97.4kDa
66.3
42.2
30.0
20.1

AMINOKETONE ASYMMETRIC REDUCTASE AND NUCLEIC ACID THEREOF

TECHNICAL FIELD

The present invention relates to an aminoketone asymmetric reductase, a nucleic acid coding the enzyme, a microorganism producing the enzyme, and a method of producing an optically active aminoalcohol using them.

BACKGROUND ART

Ephedrines have conventionally been used for sweating, alleviating fever, suppressing coughs, and so forth. Among them, d-pseudoephedrine has been known to have an anti-inflammatory effect. On the other hand, 1-ephedrine has been known to have pharmacological effects for constricting blood vessels, increasing blood pressure, sweating, and the like, and is medically in use as a sympathomimetic agent. Also, 1-ephedrine is used for curing bronchial asthma. Hence, a method of producing an optically active β-aminoalcohol including an optically active ephedrine is useful in the process of making a medicine or its intermediates, whereby an effective producing method is desired.

Conventionally used as a method of producing a β-aminoalcohol having a desirable optical activity comprises the steps of yielding a racemic β-aminoalcohol, and then producing a specific optically active substance by an optical resolution, asymmetric synthesis, or the like.

Since the racemic β-aminoalcohol has two asymmetric carbons within its molecular, however, a complicated step has been necessary for yielding a specific optically active substance.

For example, Ger. (East) 13683, Aug. 27, 1957 reported that, in the case of an optically active ephedrine which is a kind of β-aminoalcohol, erythro-1-2-methylamino-1-phenyl-1-propanol, i.e., 1-ephedrine can be produced by reducing/condensing methylamine with an optically active phenylacetylcarbinol obtained from benzaldehyde by fermentation utilizing a yeast.

It was further reported that a pseudoephedrine can be made by producing oxazoline from 1-ephedrine by acetic anhydride, then hydrolyzing it, and inverting it to its threo form, i.e., d-pseudoephedrine (U.S. Pat. No. 4,237,304).

As mentioned above, making pseudoephedrine having a desirable optical activity from 1-phenyl-2-methylamino-1-propanone necessitates a step of yielding an optically active erythro form of ephedrine and then inverting it into a threo form, thereby increasing and complicating the number of steps and lowering the yield.

Further, the above-mentioned making of pseudoephedrine yields a considerable amount of diastereomer as a byproduct when reducing a material ketone substance, whereas the diastereomer is hard to recover as a material, which has been economically disadvantageous.

On the other hand, though the method disclosed in Japanese Patent Application Laid-Open No. HEI 8-98697 can produce an optically active 2-amino-1-phenylethanol derivative from a 2-amino-1-phenylethanol compound having one asymmetric carbon atom within its molecule by using a specific microorganism, no effective method of producing a β-aminoalcohol having two asymmetric carbon atoms has been known yet.

DISCLOSURE OF THE INVENTION

In view of the above-mentioned problem inherent in the prior art, it is an object of the present invention to provide an aminoketone asymmetric reductase which can act to make, with a high yield and a high selectivity, a β-aminoalcohol having a desirable optical activity from an enantiomer mixture of an α-aminoketone compound or a salt thereof. It is another object of the present invention to provide a protein having an aminoketone asymmetric reduction activity, a nucleic acid coding the protein, a transformant transformed by the nucleic acid, a method of producing the protein by using the transformant, and uses of the transformant or protein. It is a further object of the present invention to provide a new microorganism which efficiently converts an enantiomer mixture of an α-aminoketone compound or a salt thereof into an optically active β-aminoalcohol.

The inventors conducted diligent studies in order to achieve the above-mentioned objects and, as a result, have found that using an aminoketone asymmetric reductase purified from a specific microorganism can reduce only one of enantiomers in an enantiomer mixture of an α-aminoketone compound or a salt thereof, thereby selectively producing with a high yield only one of four kinds of isomers of its corresponding β-aminoalcohol, thereby completing the present invention.

Namely, the protein of the present invention is a protein, which is an aminoketone asymmetric reductase, having an effect of producing d-pseudoephedrine by acting on 1-2-methylaminopropiophenone, and having the following physiochemical properties:

substrate: 1-2-methylaminopropiophenone
optimum pH: pH 8.1
optimum temperature: 55° C.
coenzyme: NADP
molecular weight: about 28500 Da homotetramer Also, the protein of the present invention is a protein having the amino acid sequence set forth in SEQ ID NO:1 in the Sequence Listing.

Further, the protein of the present invention is a protein derived from the protein comprising the amino acids sequence set forth in SEQ ID NO:1 in the Sequence Listing, comprising deletion, insertion, substitution or addition of one or more amino acids, and having an aminoketone asymmetric reduction activity, or a partial peptide thereof.

Here, the present invention encompasses a salt of said protein or a salt of partial peptides of said protein.

The nucleic acid of the present invention is a nucleic acid coding a protein comprising the amino acid sequence set forth in SEQ ID NO:1 in the Sequence Listing.

Also, the nucleic acids of the present invention is a nucleic acid comprising the nucleotide sequence set forth in SEQ ID NO:2 in the Sequence Listing.

Further, the nucleic acid of the present invention is a nucleic acid hybridizing under stringent conditions with the nucleic acid set forth in SEQ ID NO:2 in the Sequence Listing, and coding a protein having an aminoketone asymmetric reduction activity.

Here, the nucleic acid of the present invention may comprise a part of the nucleotide sequence set forth in SEQ ID NO:2 in the Sequence Listing.

A vector of the present invention can be obtained by introducing these nucleic acids into a plasmid or the like.

Also, a transformant of the present invention can be obtained by introducing the vector into a host. The present invention also encompasses aminoketone asymmetric reductases produced by using such a transformant, or partial peptides thereof.

The method of producing an aminoketone asymmetric reductase or a partial peptide thereof of the present invention is the method including a culturing step of culturing said transformant in which the transformant can proliferate; and a purification step of purifying an aminoketone asymmetric reductase or a partial peptide thereof from said transformant obtained by said culturing step.

Also, the method of producing an aminoketone asymmetric reductase or a partial peptide thereof of the present invention is a method including a culturing step of culturing at least one microorganism selected from the group of microorganisms belonging to the genus *Morganella, Microbacterium, Sphingobacterium, Nocardioides, Mucor, Absidia, Aspergillus, Penicillium, Grifola, Eurotium, Ganoderma, Hypocrea, Helicostylum, Verticillium, Fusarium, Tritirachium, Mortierella, Armillariella, Cylindrocarpon, Klebsiella, Aureobacterium, Xanthomonas, Pseudomonas, Mycobacterium, Sporobolomyces, Sporidiobolus*, and *Rhodococcus*, the microorganism being capable of reducing 1-2-methylaminopropiophenone so as to produce d-pseudoephedrine; and a purification step of purifying an aminoketone asymmetric reductase or a partial peptide thereof from the microorganism obtained by the culturing step.

Also, the microorganism of the present invention is a microorganism belonging to the genus *Rhodococcus* and being capable of reducing 1-2-methylaminopropiophenone so as to produce d-pseudoephedrine.

In particular, the microorganism is preferably *Rhodococcus erythropolis* MAK-34 strain (FERM BP-7451).

The method of producing an optically active aminoalcohol of the present invention is a method comprising the step of causing said protein, the partial peptide thereof, or the salt thereof to act on an enantiomer mixture of an α-aminoketone compound represented by the general formula (1):

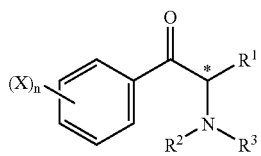

(1)

wherein X may be identical or different and is at least one kind selected from the group consisting of halogen, lower alkyl, hydroxyl optionally protected by a protecting group, nitro, and sulfonyl; n is an integer of 0 to 3; $R^1$ is lower alkyl; $R^2$ and $R^3$ may be identical or different and are at least one kind selected from the group consisting of hydrogen and lower alkyl; and * is asymmetric carbon, or a salt thereof so as to produce an optically active aminoalcohol compound represented by the general formula (2):

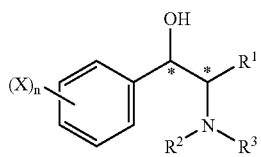

(2)

wherein X, n, $R^1$, $R^2$, $R^3$, and * are the same as those mentioned above, the resulting compound having a desirable optical activity.

Further, the method of producing an optically active aminoalcohol of the present invention is a method comprising the step of causing one microorganism selected from the group consisting of said transformant, microorganisms belonging to the genus *Rhodococcus*, and *Rhodococcus erythropolis* MAK-34 to act on an enantiomer mixture of an α-aminoketone compound represented by the general formula (1):

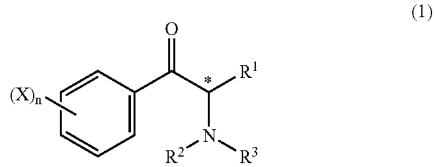

(1)

or a salt thereof so as to produce an optically active aminoalcohol compound represented by the general formula (2):

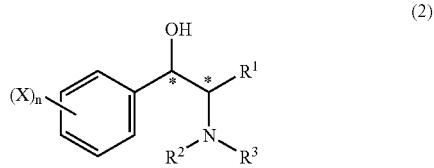

(2)

the resulting compound having a desirable optical activity.

Preferably, in the method of making an optically active aminoalcohol, a compound expressed by the general formula (3)

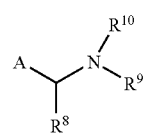

(3)

wherein A represents structural formula (Y) or (Z):

(Y)

wherein $R^4$ is hydrogen, alkyl of 1 to 3 carbon atoms optionally having a substituent, a hydrocarbon ring of 5 to 10 carbon atoms bonded with $R^8$, or a heterocyclic skeleton of a 5- to 8-membered ring including 1 to 3 heteroatoms bonded with $R^8$,

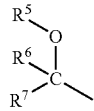

(Z)

wherein $R^5$ is hydrogen, alkyl of 1 to 3 carbon atoms, or a heterocyclic skeleton of a 5- to 8-membered ring including 1 to 3 heteroatoms bonded with R or $R^9$; $R^6$ is hydrogen, alkyl of 1 to 3 carbon atoms optionally having a substituent, a hydrocarbon ring of 5 to 10 carbon atoms bonded with $R^8$, or a heterocyclic skeleton of a 5- to 8-membered ring including 1 to 3 heteroatoms bonded with $R^5$ or $R^9$; and $R^7$ is hydrogen or alkyl of 1 to 6 carbon atoms optionally having a substituent, $R^8$ is hydrogen, carboxyl, alkyl of 1 to 6 carbon atoms optionally having a substituent, a heterocyclic skeleton of a 5- to 8-membered ring including 1 to 3 heteroatoms bonded with $R^4$, or a hydrocarbon ring of 5 to 10 carbon atoms bonded with $R^6$; $R^9$ is hydrogen, alkyl of 1 to 6 carbon atoms optionally having a substituent, acyl optionally having a substituent, or a heterocyclic skeleton of a 5- to 8-membered ring including 1 to 3 heteroatoms bonded with $R^5$ or $R^6$; and $R^{10}$ is hydrogen or optionally substituted alkyl of 1 to 6 carbon atoms;

or a pharmaceutically acceptable salt or solvate thereof is further added so as to produce an optically active aminoalcohol.

BEST MODES FOR CARRYING OUT THE INVENTION

Figure 1:
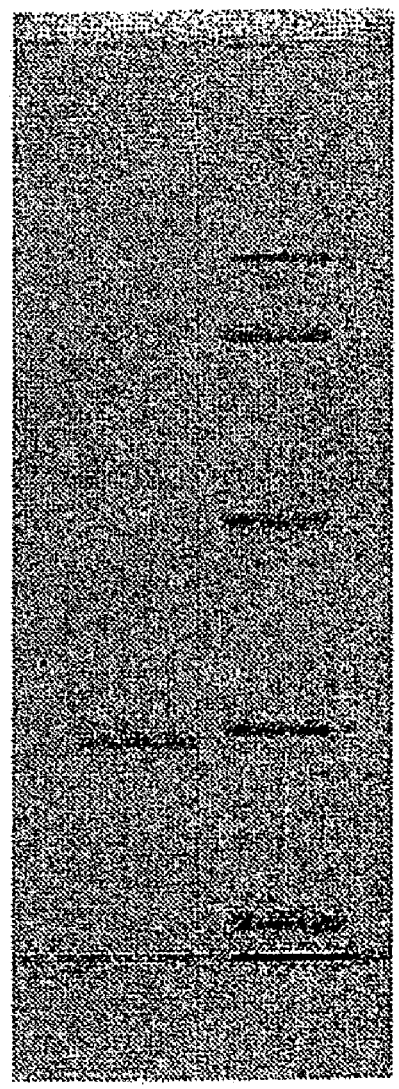
FIG. 1 is an electropherogram of the aminoketone asymmetric reductase of the present invention by SDS-PAGE.

In the following, preferred embodiments of the present invention will be explained in detail.

When nucleotides, amino acids, and the like are expressed by their abbreviations in the specification and drawings, they are based on IUPAC-IUB Commission on Biochemical Nomenclature or meanings of words conventionally used in this field. Optical isomers of amino acids will be represented by their L-form unless otherwise specified.

First, the protein of the present invention will be explained.

The protein of the present invention is a protein, which is an aminoketone asymmetric reductase, having an effect of producing d-pseudoephedrine by acting on 1-2-methylaminopropiophenone, and having the following physiochemical properties:

substrate: 1-2-methylaminopropiophenone
optimum pH: pH 8.1
optimum temperature: 55° C.
coenzyme: NADP
molecular weight: about 28500 Da homotetramer The said protein not only has an effect of producing d-pseudoephedrine by acting on 1-2-methylaminopropiophenone, but also exhibits a reduction activity with respect to 1-2-dimethylaminopropiophenone, aminoacetone, and 1-amino-2-butanone. Also, it acts on 1-amino-2-propanol, thereby producing aminoacetone.

As properties other than the physiochemical properties mentioned above, influences of various metal ions or inhibitors have been studied, whereby inhibitions by α,α'-Dipyridyl, o-Phenanthrolin, and EDTA have been confirmed.

The said protein is obtained by culturing a microorganism having an aminoketone asymmetric reduction activity, and purifying from the resulting cell.

The culturing method is not restricted in particular, and known methods can be employed as long as it can grow the microorganism in use. Normally, a liquid medium including a carbon source, a nitrogen source, and other nutrients is used. Any carbon source is usable as long as the above-mentioned microorganism can utilize it. Specifically, sugars such as glucose, fructose, sucrose, dextrin, starch, and sorbitol; alcohols such as methanol, ethanol, and glycerol; organic acids such as fumaric acid, citric acid, acetic acid, and propionic acid, and their salts; hydrocarbons such as paraffin; their mixtures; or the like can be used. Any nitrogen source is usable as long as the above-mentioned microorganism can utilize it. Specifically, ammonium salts of inorganic acids such as ammonium chloride, ammonium sulfate, and ammonium phosphate; ammonium salts of organic acids such as ammonium fumarate and ammonium citrate; nitrates such as sodium nitrate and potassium nitrate; nitrogen-containing inorganic or organic compounds such as meat extracts, yeast extracts, malt extracts, and peptone; their mixtures; or the like can be used. Nutrient sources used for normal culture such as inorganic salts, trace metal salts, and vitamins may also be added to the culture as appropriate. Substances accelerating the proliferation of the microorganism, buffer substances effective in keeping the pH of the medium, and the like may also be added to the culture if necessary.

The microorganism can be cultured under a condition suitable for its growth. Specifically, the culture can be carried out in a medium with a pH of 3 to 10, preferably 4 to 9, and a temperature of 0° C. to 50° C., preferably 20° C. to 40° C. The microorganism can be cultured under aerobic or anaerobic conditions. The culture time is preferably 10 to 150 hours, and should be determined appropriately depending on each microorganism.

From thus cultured microorganism, its culture medium is filtered or centrifuged, so as to obtain cells, which are then washed well with water or a buffer solution. The washed cells are suspended in an appropriate amount of buffer solution, and the cells are disrupted. The disruption method is not restricted in particular, examples of which include mechanical disruption methods using a mortar, a DYNO-Mill, a French press, a ultrasonic disrupter, and the like. From thus obtained homogenate of the cells, solids are removed by filtration or centrifuge, and from thus obtained cell-free extracts, the aminoketone asymmetric reductase is collected by a normal method of enzyme isolation.

Such an enzyme isolation method is not restricted in particular, and known methods can be used therefor. For example, the enzyme can be purified by salting out such as ammonium sulfate sedimentation; gel filtration by Sephadex or the like; ion-exchange chromatography using a carrier having a diethylaminoethyl group, a carboxymethyl group, or the like; hydrophobic chromatography using a carrier having a hydrophobic group such as butyl group, octyl group, or phenyl group; pigment gel chromatography; electrophoresis; dialysis; ultrafiltration; affinity chromatography; high-performance liquid chromatography; and the like.

Further, the said enzyme can be used as an immobilized enzyme. Such a method is not restricted in particular, and known methods can be used, examples of which include immobilized enzymes and enzyme-producing cells, which can be immobilized by carrier binding such as covalent binding and adsorption, crosslinking, entrapment, and the like. Condensing agents such as glutaraldehyde, hexamethylene diisocyanate, and hexamethylene diisothiocyanate may also be used as necessary. Examples of other immobilizing methods include a monomer method gelling a monomer by polymerization reaction; a prepolymer method polymerizing a molecule greater than a normal monomer; a polymer method gelling a polymer; immobilization using polyacrylamide; immobilization using natural polymers such as alginic acid, collagen, gellatin, agar, and κ-carrageenan; and immobilization using synthetic polymers such as photocurable resins and urethane polymers.

Thus purified enzyme is considered to be fully purified if a single band is confirmed by electrophoresis (SDS-PAGE or the like).

Preferably, the said microorganism having an aminoketone asymmetric reduction activity is at least one microorganism selected from the group of microorganisms belonging to the genus *Morganella, Microbacterium, Sphingobacterium, Nocardioides, Mucor, Absidia, Aspergillus, Penicillium, Grifola, Eurotium, Ganoderma, Hypocrea, Helicostylum, Verticillium, Fusarium, Tritirachium, Mortierella, Armillariella, Cylindrocarpon, Klebsiella, Aureobacterium, Xanthomonas, Pseudomonas, Mycobacterium, Sporobolomyces, Sporidiobolus,* and *Rhodococcus*. More specific examples include *Morganella morganii, Microbacterium arborescens, Sphingobacterium multivorum, Nocardioides* simplex, *Mucor ambiguus, Mucor javanicus, Mucor fragilis, Absidia lichtheimi, Aspergillus awamori, Aspergillus niger, Aspergillus oryzae, Aspergillus candidus, Aspergillus oryzae* var. *oryzae, Aspergillus foetidus* var. *acidus, Penicillium oxalicum, Grifola frondosa, Eurotium repens, Ganoderma lucidum, Hypocrea gelatinosa, Helicostylum nigricans, Verticillium fungicola* var. *fungicola, Fusarium roseum, Tritirachium oryzae, Mortierella isabellina, Armillariella mellea, Cylindrocarpon sclerotigenum, Klebsiella pneumoniae, Aureobacterium esteraromaticum, Xanthomonas sp., Pseudomonas putida, Mycobacterium smegmatis, Mycobacterium diernhoferi, Mycobacterium vaccae, Mycobacterium phlei, Mycobacterium fortuitum, Mycobacterium chlorophenolicum, Sporobolomyces salmonicolor, Sporobolomyces coralliformis, Sporidiobolus johnsonii, Rhodococcus erythropolis,* and *Rhodococcus rhodochrous*.

The said microorganism may be any strain such as a wild strain, a variant strain, or a recombinant induced by a technique such as cell fusion or gene manipulation. It will be sufficient if at least one kind of the microorganism is used.

Further, *Rhodococcus erythropolis* MAK-34 strain is listed as a new microorganism, which is one kind of microorganism having an aminoketone asymmetric reduction activity in accordance with the present invention, having a particularly effective aminoketone asymmetric reduction activity. *Rhodococcus erythropolis* MAK-34 strain is a new microorganism separated from the nature by the inventors, and was deposited with International Patent Organism Depositary, National Institute of Advanced Industrial Science and Technology (Central 6, 1-1-1 Higashi, Tsukuba, Ibaraki, Japan, 305-8566) on Feb. 15, 2001 under the accession number of FERM BP-7451.

*Rhodococcus erythropolis* MAK-34 strain has the following microbiological properties:
Taxonomic Properties
(1) Morphological Properties
cellular form: rod-shaped bacterium
cell size: 1.0×1.5 to 2.0 μm
characteristic feature: V-shaped formation
motility: −
spore: −
(2) Cultural Properties
culture temperature: 30° C.
colony form: circular, marginally erosive, protruded, slightly glossy, cream-colored gelatin liquidation: −
(3) Physiological Properties
Gram staining: +
nitrate reduction: −
citrate utilization: +
urease: +
oxidase: −
catalase: +
behavior toward oxygen: aerobic
O/F test: −
pyrazinamidase: −
pyrrolidonyl arylamidase: −
alkaline phosphatase: +
β-glucuronidase: −
β-galactosidase: −
α-glucosidase: +
N-acetyl-β-glucosaminidase: −
esculin (glucosidase): +

Usability of Carbohydrates lactose: −
maltose: +
mannose: +
benzoate: +
butane-2,3-diol: +
citraconic acid: −
D-mandelic acid: −
DL-norleucine: +
pimelic acid: −
spermine: −
(4) The whole nucleotide sequence of 16S rRNA was analyzed and was compared with database of MicroSeq.

Strains considered to be related to the above-mentioned strain and differences therefrom:
*Rhodococcus erythropolis*: 0.56%
*Rhodococcus globerulus*: 0.76%
*Tsukamurella wratislaviensis*: 2.54%
*Rhodococcus fascians*: 2.94%

The foregoing results have indicated that *Rhodococcus erythropolis* has a homology of 99.44% and is the most closely related microorganism group.

Also, the protein of the present invention is a protein comprising the amino acid sequence set forth in SEQ ID NO:1 in the Sequence Listing; and protein derived from the protein comprising the said amino acids sequence, comprising deletion, insertion, substitution or addition of one or more amino acids, and having an aminoketone asymmetric reduction activity.

The method of providing such a deletion, insertion, substitution, or addition is not restricted in particular, and known methods can be used. Examples of the methods include those described in the Japanese Biochemical Society, ed., "Sequel to Biochemical Experiment Lecture 1, Gene Study Method II", p. 105 (Susumu Hirose), Tokyo Kagaku Dojin (1986); the Japanese Biochemical Society, ed., "New Biochemical Experiment Lecture 2, Nucleic Acid III (Recombinant DNA Technique)", p. 233 (SusumuHirose), Tokyo Kagaku Dojin (1992); R. Wu, L. Grossman, ed., "Methods in Enzymology", Vol. 154, p. 350 & p. 367, Academic Press, New York (1987); R. Wu, L. Grossman, ed., "Methods in Enzymology", Vol. 100, p. 467 & p. 468, Academic Press, New York (1983); J. A. Wells et al., "Gene", Vol. 34, p. 315 (1985); T. Grundstroem et al., "Nucleic Acids Res.", Vol. 13, p. 3305 (1985); J. Taylor et al., "Nucleic Acids Res.", Vol. 13, p. 8765 (1985); R. Wu ed., "Methods in Enzymology", Vol. 155, p. 568, Academic Press, New York (1987); and A. R. Oliphant et al., "Gene", Vol. 44, p. 177 (1986). Specific examples include site-directedmutagenesis (site-specified mutagenesis), Kunkel method, and dNTP [αS] method (Eckstein method) utilizing a synthetic oligonucleotide or the like, and region-specific mutagenesis using sulfurous acid, nitrous acid, or the like.

There are cases where sugar chains are added to many proteins, whereby the addition of sugar chains can be regulated by substituting one or more amino acids. Therefore, the protein of the present invention encompasses proteins having the above-mentioned sugar chains regulated in the amino acid sequence set forth in SEQ ID NO:1 in the Sequence Listing as long as they have the above-mentioned aminoketone asymmetric reduction activity.

Thus obtained protein of the present invention can be modified by amino acid residues contained therein by a chemical technique, or can be altered into its derivatives by modification or partial decomposition using enzymes such as peptidases, e.g., pepsin, chymotrypsin, papain, bromelain, endopeptidase, and exopeptidase.

When the protein is produced by gene recombination, it may be expressed as a fusion protein, and then be converted/processed in vivo or in vitro into one having a biological activity substantially the same as that of a natural aminoketone asymmetric reductase. In this case, while fusion production methods commonly employed in genetic engineering can be used, such a fusion protein can be purified by affinity chromatographyor the like by utilizing its fused part. Modifications, alterations, and the like of the structure of protein can be carried out, for example, with reference to the Japanese Biochemical Society, ed., "New Biochemical Experiment Lecture 1, Protein VII, Protein Engineering", Tokyo Kagaku Dojin (1993) and by methods described therein, methods described in literatures cited therein, and methods substantially the same thereto.

Further, the present invention may be one which differs from the natural one in terms of the identity of one or more amino acid residue, and one which differs from the natural one in terms of the position of one or more amino acid residue. The present invention may encompass deletion analogues lacking one or more (e.g., 1 to 80, preferably 1 to 60, more preferably 1 to 40, further preferably 1 to 20, particularly 1 to 10) amino acid residues peculiar to the natural aminoketone asymmetric reductase, substitution analogues having one or more (e.g., 1 to 80, preferably 1 to 60, more preferably 1 to 40, further preferably 1 to 20, particularly 1 to 10) peculiar amino acid residues substituted by other residues, and addition analogues having one or more (e.g., 1 to 80, preferably 1 to 60, more preferably 1 to 40, further preferably 1 to 20, particularly 1 to 10) amino acid residues added thereto. Those having a domain structure which is characteristic of the natural aminoketone asymmetric reductase may be included. Also, those having the same quality of aminoketone asymmetric reductase activity may be mentioned.

The present invention encompasses all of the mutants such as those mentioned above as long as they maintain a domain structure which is characteristic of the natural aminoketone asymmetric enzyme. It also seems that the present invention may encompass those having a primary structure conformation substantially equivalent to that of the natural aminoketone asymmetric reductase or a part thereof, and those having a biological activity substantially equivalent to that of the natural aminoketone asymmetric reductase. Further, the present invention may encompass one of naturally occurring mutants. Such an aminoketone asymmetric reductase of the present invention can be separated/purified as will be explained later. On the other hand, the present invention encompasses a DNA sequence coding the above-mentioned polypeptide, polypeptides of the aminoketone asymmetric reductase having all or a part of natural characteristics, and a DNA sequence coding analogues or derivatives thereof. The nucleotide sequence of the aminoketone asymmetric reductase can be modified (e.g., by addition, removal, substitution, etc.), and thus modified ones may be included.

The nucleic acid of the present invention will now be explained.

The nucleic acid of the present invention is a nucleic acid coding a protein comprising the amino acid sequence set forth in SEQ ID NO:1 in the Sequence Listing.

Since there are a plurality of nucleotide sequences (codons) coding one amino acid, there are a number of nucleic acid coding the protein comprising the amino acid sequence set forth in SEQ ID NO:1 in the Sequence Listing. Such nucleic acids are also included in the nucleic acid of the present invention. Here, "coding a protein" means to encompass those having a nucleotide sequence coding one of two complementary chains of DNA if DNA has two chains, whereby the nucleic acid of the present invention also encompasses nucleic acids comprising nucleotide sequences directly coding the amino acid sequence set forth in SEQ ID NO:1 in the Sequence Listing, or nucleic acids comprising nucleotide sequences complementary thereto.

Also, the nucleic acid of the present invention is a nucleic acid comprising the nucleotide sequence set forth in SEQ ID NO:2 in the Sequence Listing.

The nucleotide sequence set forth in SEQ ID NO:2 in the Sequence Listing is the nucleotide sequence of DNA obtained by extracting genome DNA from the above-mentioned microorganism, and then subjecting it to PCR (Polymerase Chain Reaction) using a synthetic oligonucleotide primer designed according to the amino acid sequence of aminoketone asymmetric reductase.

Though the method of extracting genome DNA from the above-mentioned microorganism is not restricted in particular, for example, cells of microoganism obtained by culture (e.g., *Rhodococcus erythropolis* MAK-34 strain) are disrupted, chromosome DNA is centrifuged by a normal method, RNA is thereafter decomposed and removed, and deproteinization is carried out, so as to purify DNA. For these operations, reference can be made to "Plant Biotechnology Experiment Manual", Noson-Bunkasha, p. 252. Any microorganism capable of producing an aminoketone asymmetric reductase belonging to the genus *Rhodococcus* can favorably be used as a DNA source.

As the method of preparing the oligonucleotide primer used in the above-mentioned PCR, known methods can be used, whereby the synthetic oligonucleotide primer is prepared according to amino acid information of aminoketone asymmetric reductase.

For example, the synthetic oligonucleotide primer can be prepared according to amino acid information of a purified aminoketone asymmetric reductase obtained from the above-mentioned microorganism capable of producing an aminoketone asymmetric reductase. In general, a degenerated primer or the like is prepared according to the amino acid sequence. The primer can be prepared by methods known in this field. For example, it can be synthesized by phosphodiester method, phosphotriester method, phoshoramidite method, or the like using a DNA autosynthesizer. Specifically, an aminoketone asymmetric reductase is purified from cells obtained by culturing *Rhodococcus erythropolis* in a nutrient medium, and is segmented by a peptide hydrolase if necessary, so as to collect information about the amino acid sequence of the enzyme. From thus obtained information of the amino acid sequence, a preferable synthetic oligonucleotide primer is prepared. Using this primer, PCR is carried out with the genome DNA of aminoketone asymmetric reductase employed as a template. The PCR reaction can be carried out by known methods in this field, methods substantially the same thereto, or altered methods. For example, it can be carried out according to methods described in R. Saiki, et al., Science, Vol. 230, pp. 1350 (1985); R. Saiki, et al., Science, Vol. 239, pp. 487 (1988); and Henry A. Erlich, PCR Technology, Stockton Press. The reaction can be carried out, for example, by utilizing commercially available kits and reagents.

The resulting amplified DNA fragments is sequenced, is confirmed to include a sequence homologous to the amino acid sequence of the purified enzyme, and is labeled with an isotope, so as to be used as a probe for subsequent experiments and the like. The nucleotide sequence can be determined by dideoxy methods such as M13 dideoxy method, for example, Maxam-Gilbert method, and the like. The determination can be carried out by using commercially available sequencing kits such as Taq dye primer cycle sequencing kit, for example, automatic sequencer such as fluorescent DNA sequencer, for example, and the like. For labeling the probe or the like with a radioisotope or the like, commercially available labeling kits such as random primed DNA labeling kit (Boehringer Mannhaim) can be used, for example.

The gene of aminoketone asymmetric reductase of the present invention can be cloned by the following method, for example. Specifically, for example, the genetic engineering can be carried out by methods described in T. Maniatis et al., "Molecular Cloning", 2nd Ed., Cold Spring Harbor Laboratory, Cold Spring Harbor, N. T. (1989); the Japanese Biochemical Society, ed., "Sequel to Biochemical Experiment Lecture 1, Gene Study Method II", Tokyo Kagaku Dojin (1986); the Japanese Biochemical Society, ed., "New Biochemical Experiment Lecture 2, Nucleic Acid III (Recombinant DNA Technique)", Tokyo Kagaku Dojin (1992); R. Wuetal., ed., "Methods in Enzymology", Vol. 68, Academic Press, New York (1980); R. Wu et al., ed., "Methods in Enzymology", Vol. 100 & 101, Academic Press, New York (1983); R. Wu et al., ed., "Methods in Enzymology", Vol. 153, 154 & 155, Academic Press, New York (1987); and the like; methods described in literatures cited therein, and methods substantially the same thereto, or modified methods. These techniques may be those originally altering and improving known techniques in conformity to the object of the present invention.

Also, the nucleic acids of the present invention is a nucleic acid hybridizing under stringent conditions with the nucleic acid comprising the nucleotide sequence set forth in SEQ ID NO:2 in the Sequence Listing, and coding a protein having an aminoketone asymmetric reduction activity.

Here, "hybridizing under stringent conditions" in the present invention means that two DNA fragments hybridize with each other under the hybridization condition described in J. Sambrook, et al., "Expression of cloned genes in *E. coli*", Molecular Cloning: A laboratory manual (1989), Cold Spring Harbor Laboratory Press, New York, USA, 9.47–9.62 and 11.45–11.61.

More specifically, "stringent conditions" refers to performing hybridization by 6.0×SSC at about 45° C. For selecting stringency, the salt concentration in a washing step is selectable, for example, within the range from a low stringency of about 2.0×SSC at 50° C. to a high stringency of about 6.0×SCC at 50° C. Further, the temperature of the washing step can be raised from the room temperature of about 22° C. under a low stringency condition to about 65° C. under a high stringency condition.

Further, the nucleic acid of the present invention is a nucleic acid comprising apart of the nucleotide sequence set forth in SEQ ID NO:2 in the Sequence Listing.

The vector of the present invention will now be explained.

The vector of the present invention is a vector containing the above-mentioned nucleic acid.

Here, any plasmid may be used for integrating the said nucleic acid as long as it can express a protein coded by the said nucleic acid in a host cell (e.g., prokaryotic cell host such as *Escherichia coli* or *Bacillus subtilis*, or eukaryotic cell host such as yeast) commonly used in the genetic engineering. In such a sequence, a codon suitable for expression in a selected host cell can be introduced, or a restriction enzyme site can be provided. Also, it can contain regulatory sequences, enhancer sequences, and the like for making it easier to express the aimed gene; linkers, adapters, and the like useful for binding the aimed gene; and sequences regulating the resistance to antibiotics and the like or regulating metabolism, thus being useful for selecting the cell and the like.

Examples of the promoter contained in the said plasmid include tryptophan (trp) promoter, lactose (lac) promoter, tryptophan/lactose (tac) promoter, lipoprotein (lpp) promoter, and λ phage PL promoter in plasmids using *Escherichia coli* as their host; and GAL1 and GAL10 promoters in plasmids using yeast as their host.

Examples of plasmids using *Escherichia coli* as their host include pBR322, pUC18, pUC19, pUC118, pVC119, pSP64, pSP65, pTZ-18R/-18U, pTZ-19R/-19U, pGEM-3, pGEM-4, pGEM-3Z, pGEM-4Z, pGEM-5Zf(–), and pBluescript KS™ (Stratagene) Examples of plasmids suitable for expression in *Escherichia coli* include pAS, pKK223 (Pharmacia), pMC1403, pMC931, and pKC30.

Examples of plasmids using yeast as a host include YIp type vector, YEp type vector, YRp type vector, YCp type vector, and pGPD-2.

When a host cell is *Escherichia coli*, examples of the host cell include those derived from *Escherichia coli* K12 strain, specifically, NM533, XL1-Blue, C600, DH1, HB101, JM109, and the like.

In the genetic engineering technique of the present invention, restriction enzyme, reverse transcriptase, DNA modification enzyme/DNase for modifying or transforming DNA fragments into a structure suitable for cloning, DNA polymerase, terminal nucleotidyl transferase, DNA ligase, and the like which have been known in this field or universally in use can be employed. Examples of the restriction enzyme include those described in R. J. Roberts, Nucleic Acids Res., Vol. 13, r165 (1985); S. Linn et al., ed., Nucleases, p. 109, Cold Spring Harbor Lab., Cold Spring Harbor, N.Y., 1982. Examples of reverse transcriptase include those derived from mouse Moloney leukemia virus (MMLV) and those derived from avian myeloblastosis virus (AMV), and RNase H deletion mutant can be used favorably in particular. Examples of DNA polymerase include *Escherichia coli* DNA polymerase, Klenow fragments which are derivatives thereof, *Escherichia coli* phage T4 DNA polymerase, Escherichia coli phage T7 DNA polymerase, and heat-resistant bacteria DNA polymerase.

An example of the terminal nucleotidyl transferase is TdTase which add deoxynucleotide (dNMP) to 3'-OH terminal described in R. Wu et al. ed., "Methods in Enzymology", Vol. 100, p. 96, Academic Press, New York (1983).

Examples of the DNA modification enzyme/DNase include exonuclease and endonuclease. Specific examples include snake venom phosphodiesterase, spleen phosphodiesterase, *Escherichia coli* DNA exonuclease I, *Escherichia coli* DNA exonuclease III, *Escherichia coli* DNA exonuclease VII, λ exonuclease, DNase I, nuclease S1, and *Micrococcus* nuclease.

Examples of DNA ligase include *Escherichia coli* DNA ligase and T4 DNA ligase.

Examples of the vector suitable for constructing a DNA library by cloning DNA gene include plasmid, λ phage, cosmid, P1 phage, F factor, and YAC. In particular, vectors derived from λ phage are preferable, specific examples of which include Charon 4A, Charon 21A, λgt10, λgt11, λDASHII, λFIXII, λEMBL3, and λZAPII™ (Stratagene).

By introducing the vector of the present invention into a host cell such as those mentioned above, a transformant of microorganism, animal cell, or the like which can produce the aminoketone asymmetric reductase of the present invention can be obtained. The present invention can also encompass such a transformant.

The transforming method is not restricted in particular, and known methods can be used therefor, examples of which include a method in which a protoplast cell prepared by using an appropriate cell wall digesting enzyme is brought into contact with DNA in the presence of calcium chloride, polyethyleneglycol, and the like, calcium phosphate method, lipofection method, electropolation method (e.g., E. Neumann et al., "EMBO J", Vol. 1, pp. 841 (1982), microinjection method, and a method of implantation with a gene gun.

Using the said transformant, the protein of the present invention can also be produced as a recombinant protein. The present invention encompasses methods of making such a recombinant protein as well.

When the protein of the present invention is obtained as an inclusion body, it may be subjected to solubilizing treatment, e.g., processing in the presence of a denaturating agent such as guanidine hydrochloride or urea and, if necessary, a reducing agent such as 2-mercaptomethanol or dithiothreitol, so as to be purified as an active form enzyme. As the enzyme, enzyme-producing cells can be used as they are.

An example of the transformant used for producing the said recombinant protein is *Escherichia coli* (JM109) MAK-EX41 (BP-7452) possessing a vector (pKK223-3) having an aminoketone asymmetric reductase gene introduced therein. MAK-EX41 has been deposited with National Institute of Bioscience and Human-Technology (NIBH), National Institute of Advanced Industrial Science and Technology, Ministry of Economy, Trade, and Industry, at 1-1-3 Higashi, Tsukuba, Ibaraki (postal code 305-8566) since Feb. 15, 2001 (original deposit date) according to the Budapest Treaty and kept under the accession number BP-7452.

The method of producing an optically active aminoalcohol in accordance with the present invention will now be explained.

The method of producing an optically active aminoalcohol of the present invention is a method of producing an optically active aminoalcohol comprising the step of causing the said protein to act on an enantiomer mixture of an α-aminoketone compound represented by the general formula (1):

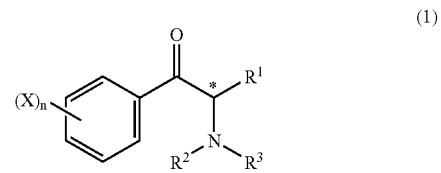

wherein X may be identical or different and is at least one kind selected from the group consisting of halogen, lower alkyl, hydroxyl optionally protected by a protecting group, nitro, and sulfonyl; n is an integer of 0 to 3; $R^1$ is lower alkyl; $R^2$ and $R^3$ may be identical or different and are at least one kind selected from the group consisting of hydrogen and lower alkyl; and * is asymmetric carbon, or a salt thereof so as to produce an optically active aminoalcohol compound represented by the general formula (2):

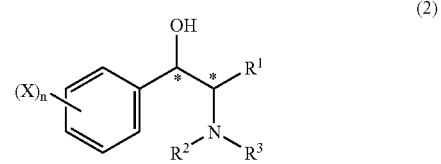

wherein X, n, $R^1$, $R^2$, $R^3$, and * are the same as those mentioned above, the resulting compound having a desirable optical activity.

First, the α-aminoketone compound represented by the general formula (1) in accordance with the present invention will be explained.

This is an enantiomer mixture of the α-aminoketone compound expressed by the general formula (1) or a salt thereof, wherein X may be identical or different and is at least one kind selected from the group consisting of halogen, lower alkyl, hydroxyl optionally protected by a protecting group, nitro, and sulfonyl; n is an integer of 0 to 3; $R^1$ is lower alkyl; $R^2$ and $R^3$ may be identical or different and are at least one kind selected from the group consisting of hydrogen and lower alkyl; and * is asymmetric carbon.

In the following, substituent X included in the said α-aminoketone compound will be explained. Examples of the said halogen include fluorine, chlorine, bromine, and iodine.

The lower alkyl is preferably an alkyl of 1 to 6 carbon atoms, examples of which include methyl, ethyl, propyl, isopropyl, butyl, isobutyl, s-butyl, t-butyl, pentyl, isopentyl, and hexyl. These may be linear or branched structures. These optionally have halogen such as fluorine or chlorine, hydroxyl, alkyl, amino, or alkoxy as a substituent.

Examples of the protective group for the optionally protected hydroxyl include those removable when treated with water, those removable by an acid or weak alkali, those removable by hydrogenation, and those removable by Lewis acid catalysts, thiourea, and the like, specific examples of which include acyl optionally having a substituent, silyl optionally having a substituent, alkoxyalkyl, lower alkyl optionally having a substituent, benzyl, p-methoxybenzyl, 2,2,2-trichloroethoxycarbonyl, allyloxycarbonyl, and trityl.

Examples of the said acyl include acetyl, chloroacetyl, dichloroacetyl, pivaloyl, benzoyl, and p-nitrobenzoyl. These optionally have hydroxyl, alkyl, alkoxy, nitro, halogen, and the like as a substituent. Examples of the said silyl include trimethylsilyl, t-butyldimethylsilyl, and triarylsilyl. These optinally have alkyl, hydroxyl, alkoxy, nitro, halogen, and the like as a substituent. Examples of the said alkoxyalkyl include methoxymethyl and 2-methoxyethoxymethyl. The lower alkyl encompasses alkyl of 1 to 6 carbon atoms, examples of which include methyl, ethyl, propyl, isopropyl, butyl, isobutyl, s-butyl, t-butyl, pentyl, isopentyl, and hexyl. These may be linear or branched structures. These optionally have halogen such as fluorine or chlorine, hydroxyl, alkyl, amino, or alkoxy as a substituent.

The said X may be nitro or sulfonyl, a specific example of which includes methylsulfonyl.

The number n of the said X is an integer of 0 to 3, preferably 0.

$R^1$ in the said general formula (1) is lower alkyl. Such lower alkyl is preferably alkyl of 1 to 6 carbon atoms, examples of which include methyl, ethyl, propyl, isopropyl, butyl, isobutyl, s-butyl, t-butyl, pentyl, isopentyl, and hexyl. These may be linear or branched structures.

$R^2$, $R^3$ indicate hydrogen or lower alkyl. The said lower alkyl encompasses alkyl of 1 to 6 carbon atoms, examples of which include methyl, ethyl, propyl, isopropyl, butyl, isobutyl, s-butyl, t-butyl, pentyl, isopentyl, and hexyl. These may be linear or branched structures.

Examples of the salt of the said α-aminoketone compound include inorganic acid salts such as hydrochloride, sulfate, nitrate, phosphate, and carbonate, and organic acid salts such as acetate and citrate.

The said α-aminoketone compound can easily be synthesized by halogenation, e.g., bromination, of the a carbon of its corresponding 1-phenylketone derivative and then substituting the halogen such as bromine with amine (Ger. (East) 11,332, Mar. 12, 1956).

Further, the method of producing an optically active aminoalcohol of the present invention is a method of producing an optically active aminoalcohol comprising the step of causing one microorganism selected from the group consisting of the said transformant, microorganisms belonging to the genus *Rhodococcus*, and *Rhodococcus erythropolis* MAK-34 to act on an enantiomer mixture of an α-aminoketone compound represented by the general formula (1):

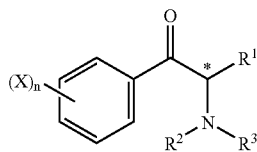

(1)

so as to produce an optically active aminoalcohol compound represented by the general formula (2):

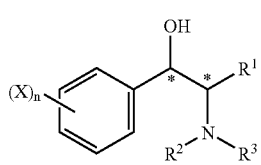

(2)

the resulting compound having a desirable optical activity.

The protein of the present invention is as mentioned above.

Namely, the protein of the present invention is a protein, which is an aminoketone asymmetric reductase, having an effect of producing d-pseudoephedrine by acting on 1-2-methylaminopropiophenone, and having the following physiochemical properties:
substrate: 1-2-methylaminopropiophenone
optimum pH: pH 8.1
optimum temperature: 55° C.
coenzyme: NADP
molecular weight: about 28500 Da homotetramer Also, the said protein encompasses a protein comprising the amino acid sequence set forth in SEQ ID NO:1 in the Sequence Listing; and protein derived from the protein comprising the said amino acids sequence, comprising deletion, insertion, substitution or addition of one or more amino acids.

In the method of producing an optically active aminoalcohol in accordance with the present invention, the said transformant, microorganisms belonging to the genus *Rhodococcus*, or *Rhodococcus erythropolis* MAK-34 strain (FERM BP-7451) may directly be added in place of the said protein into the reaction, so as to make an optically active aminoalcohol.

The optically active aminoalcohol represented by the general formula (2) in accordance with the present invention will now be explained.

X, n, $R^1$, $R^2$, $R^3$, and * in the said general formula (2) are the same as those in the said general formula (1). An example of β-aminoalcohol having a desirable optical activity is (1S, 2S) aminoalcohol.

In an example of condition under which the said reaction is carried out, a transformed microorganism shaking-cultured in a liquid medium is collected, an aqueous solution of aminoketone (0.1% to 10% concentration) is added to thus obtained cells, and the reaction is performed for several hours to 1 day at a temperature of 10° C. to 40° C. while adjusting pH to 6 to 8. After the reaction is completed, the cells are separated, and the product in the reaction solution is isolated, whereby an optically active aminoalcohol can be obtained. Here, the processed cells (dried cells, immobilized cells, or the like) of the transformed microorganism, the immobilized enzyme, or the like can be handled in the same manner.

In the method of producing an optically active aminoalcohol in accordance with the present invention, a compound represented by the general formula (3)

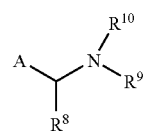

(3)

wherein A represents structural formula (Y) or (Z):

(Y)

wherein $R^4$ is hydrogen, alkyl of 1 to 3 carbon atoms optionally having a substituent, a hydrocarbon ring of 5 to 10 carbon atoms bonded with $R^8$, or a heterocyclic skeleton of a 5- to 8-membered ring including 1 to 3 heteroatoms bonded with $R^8$,

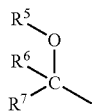

(Z)

wherein $R^5$ is hydrogen, alkyl of 1 to 3 carbon atoms, or a heterocyclic skeleton of a 5- to 8-membered ring including 1 to 3 heteroatoms bonded with $R^6$ or $R^9$; $R^6$ is hydrogen, alkyl of 1 to 3 carbon atoms optionally having a substituent, a hydrocarbon ring of 5 to 10 carbon atoms bonded with $R^8$, or a heterocyclic skeleton of a 5- to 8-membered ring including 1 to 3 heteroatoms bonded with $R^5$ or $R^9$; and $R^7$ is hydrogen or alkyl of 1 to 6 carbon atoms optionally having a substituent, $R^8$ is hydrogen, carboxyl, alkyl of 1 to 6 carbon atoms optionally having a substituent, a heterocyclic skeleton of a 5- to 8-membered ring including 1 to 3 heteroatoms bonded with $R^4$, or a hydrocarbon ring of 5 to 10 carbon atoms bonded with $R^6$; $R^9$ is hydrogen, alkyl of 1 to 6 carbon atoms optionally having a substituent, acyl optionally having a substituent, or a heterocyclic skeleton of a 5- to 8-membered ring including 1 to 3 heteroatoms bonded with $R^5$ or $R^6$; and $R^{10}$ is hydrogen or optionally substituted alkyl of 1 to 6 carbon atoms;

or a pharmaceutically acceptable salt or solvate thereof may further be added to the reaction so as to produce an optically active aminoalcohol, whereby the optically active aminoalcohol can be produced more efficiently.

In the said general formula (3), alkyl of 1 to 3 carbon atoms may be either linear or branched, specific examples of which include methyl, ethyl, n-propyl, and isopropyl. The alkyl of 1 to 6 carbon atoms may be either linear or branched, specific examples of which include methyl, ethyl, n-propyl, isopropyl, n-butyl, i-butyl, s-butyl, t-butyl, pentyl, and hexyl. Examples of the hydrocarbon ring of 5 to 10 carbon atoms include cyclopentyl, cyclohexyl, cycloheptyl, cyclooctyl, cyclononyl, and cyclodecanyl.

In the heterocyclic skeleton of a 5- to 8-membered ring including 1 to 3 heteroatoms, examples of the heteroatoms include nitrogen, oxygen, and sulfur, preferably nitrogen and oxygen in particular, whereas examples of the heterocyclic skeleton of the 5- to 8-membered ring include pyrrolidine, piperidine, imidazolidine, piperazine, tetrahydrofuran, tetrahydropyran, tetrahydrothiophene, and morpholine.

Examples of alkyloxycarbonyl of 1 to 6 carbon atoms include methyloxycarbonyl, ethyloxycarbonyl, isopropyloxycarbonyl, isobutyloxycarbonyl, and t-butyloxycarbonyl. Examples of acyl include formyl, acetyl, propionyl, butyryl, isobutyryl, pivaloyl, benzoyl, and valeryl. When the said alkyl of 1 to 3 carbon atoms or 1 to 6 carbon atoms, alkyloxycarbonyl of 1 to 6 carbon atoms, or acyl has substituents, the kinds, positions, and numbers of substituents are not restricted in particular, whereas examples of the substituents include halogen such as fluorine and chlorine, hydroxyl, alkyl, carboxyl, amino, alkoxy, nitro, and aryl. Examples of the pharmaceutically acceptable salt include inorganic acid salts such as hydrochloride, sulfate, nitrate, phosphate, and carbonate; organic acid salts such as acetate and citrate; inorganic alkali salts of Na, K, Mg, Ca, ammonia, and the like; and organic alkali salts of triethylamine, cyclohexylamine, and the like.

Examples of the compound represented by the general formula (3) include 1-acetylamino-2-hydroxypropane, 1-methylamino-2-hydroxypropane, 1-amino-2-oxopropane, 1-amino-2-hydroxycyclopentane, 1-amino-2,3-dihydroxypropane, L-threonine, 4-amino-3-hydroxybutanoic acid, 1-amino-2-oxocyclohexane, morpholine, 3-hydroxypyrrolidine, 3-hydroxypiperidine, 2-aminomethyltetrahydrofuran, 1-(2-hydroxypropyl)amino-2-hydroxypropane, 1-t-butyloxycarbonylamino-2-hydroxypropane, 2-amino-3-hydroxybutane, DL-serine, 1-amino-2-hydroxypropane, 1-amino-2-hydroxybutane, and 1-amino-2-hydroxycyclohexane. Among them, compounds having asymmetric carbon may be either an optically active substance or a racemic substance unless otherwise specified.

Adding these activity inducers into the medium induces the activity of the microorganism, whereby the subsequent production of an optically active β-aminoalcohol proceeds more efficiently than in the case without the addition. The activity inducers may be used one by one or in mixtures of two or more. The amount of addition of such an activity inducer is preferably 0.01 to 10 wt % with respect to the medium.

As explained in the foregoing, a genetic structure coding a natural aminoketone asymmetric reductase, such as a natural aminoketone asymmetric reductase derived from *Rhodoccocus erythropolis* or a protein having an activity substantially equivalent thereto is clarified, so that a drastic development is expected in uses such as a host cell transformed by DNA containing a nucleotide sequence coding the said protein, a method of producing a protein using the host cell, and the producing of an optically active aminoalcohol using the protein and host cell, and the aminoketone asymmetric reductase itself can be altered so as to increase its enzymatic activity.

EXAMPLES

In the following, the present invention will be explained more specifically with reference to Examples, which do not restrict the present invention.

Example 1

(Purification of Aminoketone Asymmetric Reductase)

*Rhodococcus erythropolis* MAK-34 were planted in a test tube containing 5 ml of a medium having a composition (pH 7.0) comprising 1% of glucose, 0.3% of dipotassium hydrogenphosphate, 0.02% of magnesium sulfate heptahydrate, 1.5% of peptone, 0.2% of sodium chloride, and 0.1% of yeast extract, and were shaking-cultured at 28° C. for 3 days, and then were inoculated into 500 ml of a medium having the same composition, the shaking-culture was carried out at 28° C. for 3 days. Thus obtained preculture medium was inoculated into 50 l of a medium with addition of 0.1% of 1-amino-2-hydroxypropane to the above-mentioned composition, and the culture was carried out at 28° C. for 2 days.

Thus obtained culture medium was treated with a centrifuge, whereby 3785 g of wet cells were obtained. To 1 kg of the cells, 1000 ml of 10 mM Tris-hydrochloric acid buffer solution (pH 8.5) containing 10% of glycerol, 1 mM of nickel chloride, and 1 mM of nicotinic acid were added. The resulting mixture was ultrasonically disrupted for 90 to 100 minutes, and then was ultracentrifuged (at 33,000 rpm for 60 minutes), whereby 759 ml of cell-free extract was obtained. This cell-free extract was dialyzed with the above-mentioned buffer solution. Thus obtained 770 ml of enzyme solution was loaded onto a DEAE-Sephacel column (5.6×20 cm), and were eluted with a linear concentration gradient (0.15–0.8 M) of sodium chloride. Thus eluted 173 ml of enzymatically active fraction were dialyzed with the above-mentioned buffer solution. Thus obtained 173 ml of enzyme solution were loaded onto a Mono Q HR 10/10 column (1.0×10 cm), and were eluted with a linear concentration gradient (0–0.6 M) of sodium chloride. Thus eluted 28 ml of enzymatically active fraction were dialyzed with the above-mentioned buffer solution excluding nicotinic acid. Thus obtained 28 ml of enzyme solution were loaded onto HiTrap Blue (1 ml), and the column was washed with a 10 mM Tris-hydrochloric acid buffer solution (pH 8.5) containing 10% of glycerol, 1 mM of nickel chloride, 2 mM of nicotinic acid, 1.0 M of sodium chloride, and 0.024% of $NADP^+$, whereby 8.7 ml of eluted enzymatically active fraction were obtained. Thus obtained 8.7 ml of enzyme solution, with 1.2M of ammonium sulfate added thereto, were loaded onto Phenyl Superose HR 5/5 (0.5×5 cm), and were eluted with a linear concentration gradient (1.2–0 M) of ammonium sulfate. Thus eluted 2.12 ml of enzymatically active fraction were ultra filtrated with Amicon YM10. Thus obtained 150 μl of enzyme concentrate were loaded onto Superose 12 HR 10/30 (1.0×30 cm), and were eluted with a 10 mM Tris-hydrochloric acid buffer solution (pH 8.5) containing 10% of glycerol, 1 mM of nickel chloride, 1 mM of nicotinic acid, and 0.15 M of sodium chloride. Thus eluted 1.45 ml of enzymatically active fraction were dialyzed with a 10 mM Tris-hydrochloric acid buffer solution (pH8.5) containing 10% of glycerol, 1 mM of nickel chloride, and 1 mM of nicotinic acid, whereby a purified enzyme solution containing 293 μg of the purified enzyme was obtained.

Properties of thus purified aminoketone asymmetric reductase are shown in the following:

(1) Substrate Specificity and Enzyme Activity

While 10 μl of 1 M Tris-hydrochloric acid buffer solution (pH 8.0), 25 μl of 16 mM $NADP^+$, and 215 μl of the purified enzyme solution were held at 43° C., 1 μl of 1-amino-2-hydroxypropane was added thereto, whereby aminoacetone was produced. The increase or decrease in NADPH accompanying the reaction was measured by the change in absorbance at 340 nm. In the measurement of enzyme activity, the enzyme activity by which 1 μmol of 1-amino-2-hydroxypropane was oxidized per 1 min under the following condition was defined as 1 unit (U). As a result, the whole activity was 126 mU, the specific activity was 432 mU/mg, and the activity yield was 0.22%.

It was similarly confirmed that the enzyme acted on 1-2-methylaminopropiophenone, 1-2-dimethylaminopropiophenone, and 1-amino-2-butanone.

(2) Molecular Weight

It was about 105,000 when measured by using gel filtration, and was about 28,500 when measured by using SDS polyacrylamide gel electrophoresis (FIG. 1). This indicated that the enzyme was a tetrameric protein having four subunits each having a molecular weight of about 28,500.

(3) Optimum pH

Figure 2:
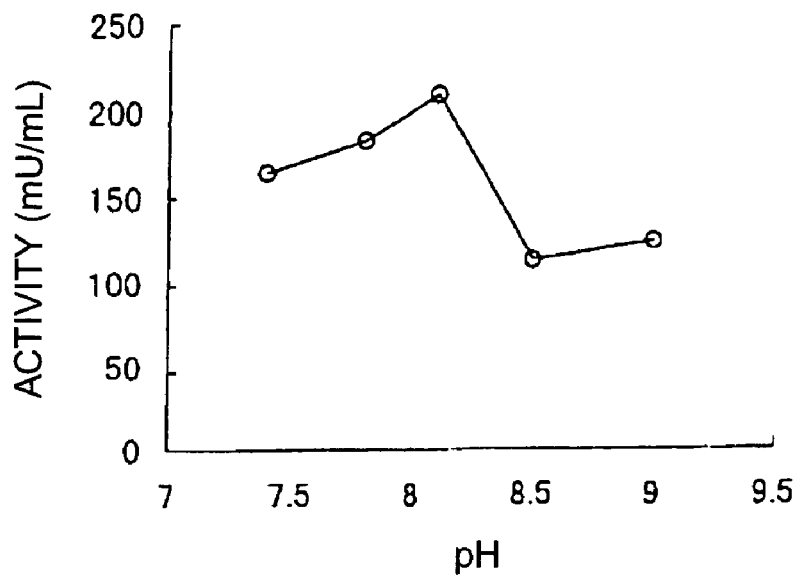
FIG. 2 is a graph showing the pH dependency of the aminoketone asymmetric reductase activity of the present invention.

Ten microliters of the purified enzyme solution, 420 μL of water, 20 μL of 1 M Tris-hydrochloric acid buffer solution, and 50 μL of 16 mM aqueous $NADP^+$ solution was mixed, and incubated at 45° C., and 2 μL of 1-amino-2-propanol were added thereto, so as to react therewith. Using a spectrophotometer, the activity was calculated from the change in absorbance at 340 nm with time (FIG. 2). As a result, the optimum pH was about 8.1.

(4) Optimum Temperature

Figure 3:
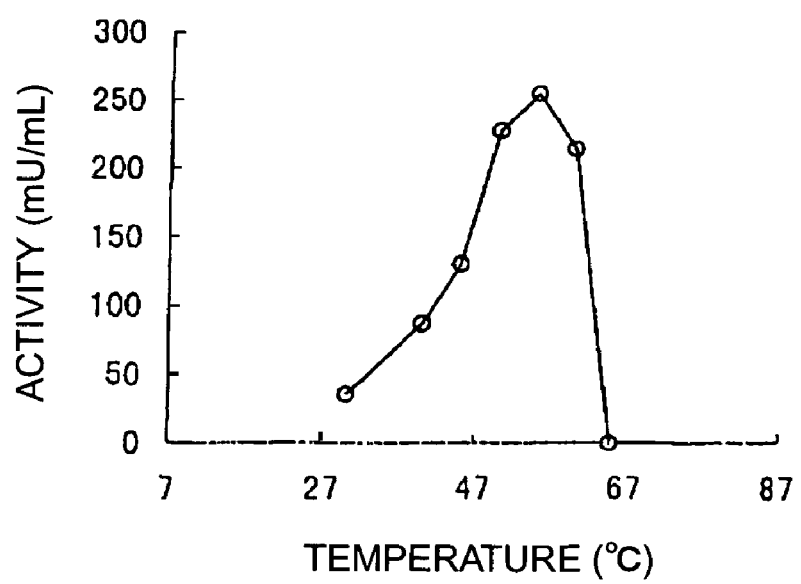
FIG. 3 is a graph showing the temperature dependency of the aminoketone asymmetric reductase activity of the present invention.

Ten microliters of the purified enzyme solution, 420 μL of water, 20 μL of 0.1 M PIPES buffer solution (pH 7.5), and 50 μL of 16 mM aqueous $NADP^+$ solution was mixed, and incubated at various temperatures, and 2 μL of 1-amion-2-propanol were added thereto, so as to react therewith. Using a spectrophotometer, the activity was calculated from the change in absorbance at 340 nm with time (FIG. 3). As a result, the optimum temperature was 55° C.

(5) Influences of Inhibitor and Metal Ion

The enzyme activity was inhibited by each of α,α'-dipyridyl at a concentration of 1 mM, o-phenanthroline at a concentration of 1 mM, and EDTA at a concentration of 1 mm.

Example 2

(Cloning of Aminoketone asymmetric Reductase Gene and Expression in *Escherichia coli*)

(1) Determination of Amino Acid Partial Sequence of Purified Enzyme

One nmol of lyophilized aminoketone asymmetric reductase (as a subunit molecular weight of about 28,500) was dissolved into 50 μl of 50 mM Tris-hydrochloric acid buffer solution (pH 8.6) containing 8 M urea, and was denatured for 1 hour at 37° C. Added thereto were 50 μl of 50 mM Tris-hydrochloric acid buffer solution (pH 8.6), so as to yield a urea concentration of 4 M. With 0.5 μl (0.006 nmol, E/S=1/167) of 12 nmol/ml lysyl endopeptidase (Wako Pure Chemical) added thereto, digestion was performed for 6 hours at 30° C. The obtained digested peptides were collected through reversed-phase column (Amersham Pharmacia Biotech), and their amino acid sequences were analyzed by ABI 476A protein sequencer. The results were as follows:

1) MFNSIEGRSVVVTGGSK (N-terminal) (SEQ ID NO: 3)
2) RLGEMTSEDMDSVFGVNVK (SEQ ID NO: 4)
3) AAQMGFIRTAAIELAPK (SEQ ID NO: 5)
4) XXILAVQAMMPXL (SEQ ID NO: 6)
5) XITINAVLPGNVITEGLDGLGQEYLDQM (SEQ ID NO: 7)

The collection condition of the above-mentioned peptide was as follows:

system: SMART system column: uRPC C2/C18 SC2.1/10 flow rate: 100 μl/min eluent: A: 0.1% TFA
B: 0.1% TFA/80% $CH_3CN$ eluting condition: gradient elution of 0–15 min (100% A)→15–75 min (100% A→100% B)

column temperature: room temperature detection wavelength: 214 nm and 280 nm.

(2) Preparation of Genome DNA

The cells (MAK-34) in the late logarithmic growth phase were collected by a centrifuge. Thus obtained cells were suspended in TES buffer (5 mM of Tris, 1 mM of EDTA, and 2.5% of sucrose; pH 8.0). This suspension, with EDTA, $H_2O$, Lysozyme, and Proteinase K added thereto, was slowly stirred for 2.5 hours at 37° C. After SDS was added thereto, the stirred lysate sample was successively treated with phenol, phenol/chloroform, and chloroform, so as to deproteinize. Added thereto were 1/10 by volume of 3 M sodium acetate and 2.5 times by volume of ethanol, and DNA was wound about a glass rod. It was successively washed with ethanol at 70%, 80%, and 90%, and air-dried DNA was dissolved in TE buffer (10 mM of Tris and 1 mM of EDTA; pH 7.8). The sample treated with RNase A was successively treated with phenol, phenol/chloroform, and chloroform, so as to deproteinize. Added thereto were 1/10 by volume of 3 M sodium acetate and 2.5 times by volume of ethanol, whereby DNA was precipitated. Thus precipitated DNA was washed with 70% ethanol, air-dried, and then dissolved into TE buffer, so as to yield a genome DNA solution (36 ng/µl).

(3) Amplification of Aminoketone Asymmetric Reductase Gene

On the basis of the amino acid sequences of the inner peptides of the aminoketone asymmetric reductase (SEQ ID NOS:3 to 7), a sense primer MAK-Sense1 (SEQ ID NO:8) corresponding to a sense strand of the N-terminal amino acid sequence and an antisense primer MAK-Anti1 (SEQ ID NO:9) corresponding to an antisense strand of the inner peptide sequence, having the following nucleotide sequences, were synthesized. Each of MAK-Sense1 and MAK-Anti1 is a degenerate primer, whereas y is T or C, s is C or G, h is T, C or A, r is A or G, m is C or A, w is A or T, n is A, C, G or T in the nucleotide sequence.

MAK-Sense1:

Met Phe Asn Ser Ile Glu Gly Arg (part of SEQ ID NO:3)

ATG TTy AAy wsn ATh GAr GGn mG (SEQ ID NO:8)

MAK-Anti1:

Met Gln Asp Leu Tyr Glu Gln Gly Leu (part of SEQ ID NO:7)

CAT yTG rTC nAr rTA yTC yTG nCC nA (SEQ ID NO:9)

Using the genome DNA of the aminoketone asymmetric reductase as a template, PCR was carried out under the following conditions. The PCR amplification was carried out according to the method described in R. Sakai, et al., Science, Vol. 230, pp. 1350 (1985); R. Sakai, et al., Science, Vol. 239, pp. 487 (1988); PCR Technology, Stockton Press (1989); or the like. About 0.6 kb of an amplified DNA fragment was obtained by the PCR amplification.

The PCR conditions were as follows:

| | |
|---|---|
| chromosome DNA (36 ng/µl) | 5 µl |
| sense primer (49 µM) | 3 µl |
| antisense primer (41 µM) | 3 µl |
| dNTP (2.5 mM each) | 4 µl |
| ExTaq polymerase (TAKARA) | 0.3 µl |
| ExTaq polymerase buffer solution | 5 µl |
| H$_2$O | 29.7 µl |
| total | 50 µl |

The temperature conditions were as follows:
94° C./4 min
94° C./1 min, 50° C./1 min, and 72° C./1.5 min: 35 cycles
72° C./10 min The nucleotide sequence of the obtained amplified DNA fragment was determined and then converted into an amino acid sequence, whereby a site identical to that of a partial amino acid sequence of an inner peptide of the aminoketone asymmetric reductase was found.

For determining the nucleotide sequence of a region whose nucleotide sequence was unknown when determining the nucleotide sequence, inverse PCR was carried out. The inverse PCR was carried out by the method described in H. Ochman, et al., Genetics, Vol. 120, pp. 621 (1988); and the like.

First, the genome DNA solution was subjected to the treatment with a restriction enzyme (BglII), phenol/chloroform treatment, and ethanol precipitation. Thus obtained DNA fragment was treated with T4DNA ligase (TAKARA), so as to perform self-ligation. The resulting product was subjected to phenol/chloroform treatment and ethanol precipitation. Using thus obtained circular DNA as a template, PCR was carried out under the following conditions while employing a sense primer (IPCR-S1) and an antisense primer (IPCR-A1) which had been designed from a part having a known nucleotide sequence. The PCR amplification yielded about 2 kb of amplified DNA fragment.

```
IPCR-A1 (for upstream)
AATACCCGGACCATTCCCAAGCCGAT      (SEQ ID NO:10)

IPCR-S1 (for downstream)
TCGAAACTTCTGGGCGTGGAAGGGTT      (SEQ ID NO:11)
```

The PCR conditions were as follows:

| | |
|---|---|
| circular DNA (500 ng) | |
| sense primer (100 µM) | 0.5 µl |
| antisense primer (100 µM) | 0.5 µl |
| dNTP (2.5 mM each) | 4 µl |
| ExTaq polymerase (TAKARA) | 0.5 µl |
| ExTaq polymerase buffer solution | 5 µl |
| H$_2$O | 39.5 µl |
| total | 50 µl |

The temperature conditions at the time of PCR were as follows:
94° C./4 min
94° C./1 min, 60° C./1 min, and 72° C./4 min: 30 cycles
72° C./10 min The nucleotide sequence of thus obtained DNA fragment was determined, whereby ORF comprising 780 bp including the previously determined nucleotide sequence was confirmed. This was converted into an amino acid sequence, and resultantly found to include the whole length of aminoketone asymmetric reductase gene (SEQ ID NO:1).

(4) Expression of Aminoketone asymmetric Reductase Gene in *Escherichia coli*

On the basis of the nucleotide sequence of the aminoketone asymmetric reductase gene elucidated in the foregoing, primers having restriction enzyme sites added thereto were designed. These sequences were as follows:

```
ExS
GATGAATTCCAAATGTTCAACTCCATTGA      (SEQ ID NO:12)
   EcoRI    Start

EsA
TGAAGCTTTCGTCGCTTGTCTTACAGTTC      (SEQ ID NO:13)
   HindIII          Stop
```

Using these primers, PCR was carried out with the genome DNA employed as a template under the following conditions. As a result, about 0.8 kb of amplified DNA fragment was obtained. The PCR conditions were as follows:

| genome DNA (36 ng/μl) | 5 μl (180 ng) |
| --- | --- |
| sense primer (100 μM) | 0.5 μl |
| antisense primer (100 μM) | 0.5 μl |
| dNTP (2.5 mM each) | 8 μl |
| LA-Taq polymerase (TAKARA) | 0.5 μl |
| LA-Taq polymerase buffer solution | 5 μl |
| $Mg^{2+}$ | 5 μl |
| $H_2O$ | 25.5 μl |
| total | 50 μl |

The temperature conditions at the time of PCR were as follows:
94° C./4 min
94° C./1 min, 60° C./1 min, and 72° C./1.5 min: 25 cycles
72° C./10 min Since thus obtained PCR product had EcoRI and HindIII restriction enzyme sites at both ends, respectively, it was purified by QIA quick PCR Purification Kit (QIAGEN), and then was treated with restriction enzymes (EcoRI and HindIII) After it was subjected to agarose electrophoresis, a band was cut out and purified by GFX PCR DNA and Gel Band Purification Kit. This was subjected to ligation (Ligation Kit, TAKARA) with plasmid pKK223-3 treated with restriction enzymes (EcoRI and HindIII), so as to construct an expression vector. Subsequently, this vector was transformed into a competent cell for *E. coli* JM 109 according to the method described in "Molecular Cloning", second ed., 1989, ed. by J. Sambrook et al., Cold Spring Harbor Laboratory Press. Thus obtained transformant was selected by colony PCR of ampicillin-resistant strain, and the transforming treatment was in conformity to calcium chloride method.

This recombinant *Escherichia coli* MAK-EX41 was shaking-cultured in 500 mL of a mixture constituted by 1% of tryptone, 0.5% of yeast extract, 0.5% of sodium chloride, 100 μg/mL of ampicillin, and 1 mM of IPTG for 16 hours at 37° C. Thus obtained cells were washed with water, and then ultrasonically treated, so as to remove insoluble matters, thereby preparing 10 mL of a crude enzyme extract. Mixed with 0.1 mL of this crude enzyme extract were 1 mg of 2-methylamino-1-phenylpropanone hydrochloride, water, 0.02 mL of 1 M Tris-hydrochloric acid buffer (pH 7.5), 10 mg of glucose, 0.1 mg of glucose dehydrogenase, and 0.1 mg of $NADP^+$, so as to yield 1 mL of a reaction solution, which was then reacted for 24 hours at 37° C. After the reaction, insoluble matters were removed from the reaction mixture, and the supernatant was subjected to HPLC analysis (μBondapakphenyl, manufactured by Waters Corporation, with a diameter of 4 mm, a length of 300 mm, an eluent of 0.05 M sodium phosphate buffer solution (containing 7% of acetonitrile), pH 6.5, a flow rate of 0.8 mL/min, and a detection wavelength of UV 220 nm), consequently, it was confirmed that 0.5 mg of pseudoephedrine was produced. Further, it was confirmed that all of thus obtained pseudoephedrine was d-pseudoephedrine as a result of HPLC analysis (SUMICHIRAL AGP, manufactured by Sumika Chemical Analysis Service Co., Ltd., with a diameter of 4 mm, a length of 150 mm, an eluent of 0.03 M sodium phosphate buffer solution, pH 7, a flow rate of 0.5 mL/min, and a detection wavelength of UV 220 nm).

*Escherichia coli* MAK-EX41 having a vector introduced therein the above-mentioned gene of aminoketone asymmetric reductase was deposited with International Patent Organism Depositary, National Institute of Advanced Industrial Science and Technology (Central 6, 1-1-1 Higashi, Tsukuba, Ibaraki, Japan, 305-8566) on Feb. 15, 2001 under the accession number of FERM BP-7452.

Example 3

(Production of d-(1S, 2S) Pseudoephedrine)

Each of the microorganisms listed in Table 1 was planted in 50 ml of a medium containing 1% of glucose, 0.5% of peptone, and 0.3% of yeast extract, and was shaking-cultured for 48 hours at 30° C. The culture medium was centrifuged to obtain the cells, which were then put into a test tube and suspended with 1 ml of 1 M sodium phosphate buffer solution (pH 7.0) added thereto. With 1 mg of dl-2-methylaminopropiophenone hydrochloride added thereto, the mixture was shaken for 24 hours at 30° C., so as to effect a reaction. After the reaction was completed, the reaction mixture was centrifuged, so as to remove the cells, and the supernatant was subjected to HPLC (μBondapak-phenyl, manufactured by Waters Corporation, with a diameter of 4 mm, a length of 300 mm, an eluent of 0.05 M sodium phosphate buffer solution (containing 7% of acetonitrile), pH 5.0, a flow rate of 0.8 mL/min, and a detection wavelength of UV 220 nm), thereby yielding an optically active pseudoephedrine.

The absolute configuration and optical purity were measured by HPLC (SUMICHIRAL AGP column manufactured by Sumika Chemical Analysis Service Co., Ltd., with a diameter of 4 mm, a length of 150 mm, 0.03 M sodium phosphate buffer solution, pH 7.0, a flow rate of 0.5 mL/min, and a detection wavelength of 220 nm). As a result, only d-pseudoephedrine was selectively obtained as shown in Tables 1 and 2.

The optical purity and amount of thus produced d-pseudoephedrine are as shown in Tables 1 and 2. In the following, all of the amounts of production will be expressed by those converted into hydrochlorides.

TABLE 1

| MICROORGANISM | | OPTICAL PURITY (%) | | | | AMOUNT OF PRODUCTION |
| --- | --- | --- | --- | --- | --- | --- |
| GENUS | IFO | d-ephedrine | l-ephedrine | d-pseudo-ephedrine | l-pseudo-ephedrine | (mg/mL) |
| *Microbacterium arborescens* | 3750 | 0 | 0 | 100 | 0 | 0.16 |
| *Klebsiella pneumoniae* | 3319 | 0 | 0 | 100 | 0 | 0.30 |
| *Aureobacterium esteraromaticum* | 3751 | 0 | 0 | 100 | 0 | 0.14 |
| *Xanthomonas* sp. | 3084 | 0 | 0 | 100 | 0 | 0.049 |

TABLE 1-continued

| MICROORGANISM | | OPTICAL PURITY (%) | | | | AMOUNT OF PRODUCTION |
| --- | --- | --- | --- | --- | --- | --- |
| GENUS | IFO | d-ephedrine | l-ephedrine | d-pseudo-ephedrine | l-pseudo-ephedrine | (mg/mL) |
| Pseudomonas putida | 14796 | 0 | 0 | 100 | 0 | 0.10 |
| Mycobacterium smegmatis | IAM 12065 | 0 | 0 | 100 | 0 | 0.24 |
| Mycobacterium diernhoferi | 14797 | 0 | 0 | 100 | 0 | 0.25 |
| Mycobacterium vaccae | 14118 | 0 | 0 | 100 | 0 | 0.28 |
| Mortierella isabellina | 8308 | 0 | 0 | 100 | 0 | 0.15 |
| Cylindrocarpon sclerotigenum | 31855 | 0 | 0 | 100 | 0 | 0.09 |
| Sporidiobolus johnsonii | 6903 | 0 | 0 | 100 | 0 | 0.07 |
| Rhodococcus erythropolis | MAK-34 | 0 | 0 | 100 | 0 | 0.30 |

TABLE 2

| MICROORGANISM | | AMOUNT OF PRODUCTION | OPTICAL PURITY (%) |
| --- | --- | --- | --- |
| GENUS | IFO | (mg/mL) | d-pseudo-ephedrine |
| Nocardioides simplex | 12609 | 0.35 | 99.0 |
| Mycobacterium phlei | 13160 | 0.27 | 95.6 |
| Mucor ambiguus | 6742 | 0.07 | 93.0 |
| Mucor javanicus | 4570 | 0.04 | 95.0 |
| Mucor fragilis | 6449 | 0.17 | 90.0 |
| Absidia lichtheimi | 4009 | 0.04 | 93.0 |
| Aspergillus awamori | 4033 | 0.18 | 93.0 |
| Aspergillus niger | 4416 | 0.11 | 90.0 |
| Aspergillus oryzae | 4177 | 0.18 | 91.0 |
| Aspergillus candidus | 5468 | 0.07 | 94.0 |
| Aspergillus oryzae | IAM 2630 | 0.08 | 92.0 |
| Aspergillus oryzae var. Oryzae | 6215 | 0.05 | 95.0 |
| Penicillium oxalicum | 5748 | 0.06 | 94.0 |
| Grifola frondosa | 30522 | 0.08 | 92.0 |
| Eurotium repens | 4884 | 0.08 | 92.0 |
| Ganoderma lucidum | 8346 | 0.05 | 92.2 |
| Hypocrea gelatinosa | 9165 | 0.27 | 92.2 |
| Helicostylum nigricans | 8091 | 0.27 | 93.2 |
| Aspergillus foetidus var. acidus | 4121 | 0.43 | 91.9 |
| Verticillium fungicola var. fungicola | 6624 | 0.10 | 92.7 |
| Fusarium roseum | 7189 | 0.40 | 89.6 |
| Tritirachium oryzae | 7544 | 0.34 | 92.0 |
| Armillariella mellea | 31616 | 0.28 | 91.0 |
| Sporobolomyces salmonicolor | 1038 | 0.14 | 95.0 |
| Sporobolomyces Coralliformis | 1032 | 0.2 | 95.0 |

Example 4

*Morganella morganii* IFO 3848 was planted in a medium containing 1% of glucose, 0.5% of peptone, and 0.3% of yeast extract, and was aerobically shaking-cultured for 48 hours at 30° C. From this culture medium, 5 ml were centrifuged, so as to yield the cells, which was air-dried. Thus obtained dry cell was suspended in 1 ml of 0.05 M Tris-hydrochloric acid buffer solution (pH 7.5). With 50 mg of glucose, 0.2 mg of glucose dehydrogenase, 0.6 mg of NADP, 0.6 mg of NAD, and 10 mg of dl-2-methylaminopropiophenone hydrochloride added thereto, the dry cell suspension was reciprocally shaken at 300 rpm at 28° C. After the reaction was carried out for 48 hours, the reaction mixture was subjected to HPLC as in the above-mentioned Example 3, whereby the amount of production and optical purity of pseudoehedrine were measured.

As a result, d-pseudoehedrine hydrochloride was produced by 0.79 mg/ml, whereas the optical purity was 100%.

Example 5

(Influence of Inducer Addition (1))

1-amino-2-hydroxypropane was added to the medium 1 (Table 3) by 5 g/L, and 5 mL of the resulting mixture were put into a test tube, which was sealed with a silicon cap and sterilized in an autoclave at 121° C. for 30 minutes. *Rhodococcus erythropolis* MAK-34 strain was planted in each of this medium and an inducer-free medium, and shaking-cultured at 30° C. for 48 hours at 300 rpm. From the resulting culture medium, 0.5 mL was centrifuged at 10000 G for 20 minutes, and the supernatant was removed, so as to leave the cells, which were then suspended with water added thereto, so as to yield a uniform suspension. Added thereto were water, a buffer solution, and 10 mg of dl-2-methylaminopropirphenone hydrochloride, so as to yield 1 mL of the mixture, which was then put into a test tube and shaken at 30° C. for 12 hours at 150 rpm, so as to effect a reaction. After the reaction was completed, the product was centrifuged, so as to remove the cells, whereas the supernatant was subjected to HPLC, so as to determine the amount of pseudoephedrine produced. (HPLC conditions: μBondapakphenyl, manufactured by Waters Corporation, with a diameter of 4 mm, a length of 300 mm, an eluent of 0.05 M sodium phosphate buffer solution (containing 7% of acetonitrile), pH 6.5, a flow rate of 0.8 mL/min, and a detection wavelength of UV 220 nm)

As a result, the amount of production of pseudoephedrine in the case of the culture with inducers added thereto was remarkably greater than that in the case of the inducer-free culture as shown in Table 4.

TABLE 3

| COMPOSITION OF MEDIUM 1 | COMPOSITION OF MEDIUM 2 |
|---|---|
| saccharose 1% | glucose 0.1% |
| corn steep liquor 0.5% | tryptone 0.5% |
| pottasium dihydrogenphosphate 0.1% | yeast extract 0.5% |
| dipottasium phosphate 0.3% | dipottasium phosphate 0.1% |
| p-aminobenzoic acid 0.01% | pH 7.0 |
| pH 7.0 | |

| COMPOSITION OF MEDIUM 3 | COMPOSITION OF MEDIUM 4 |
|---|---|
| glucose 1% | soluble starch 1% |
| bacto peptone 0.5% | glucose 0.5% |
| yeast extract 0.3% | NZ amine type A 0.3% |
| pH 7.0 | tryptone 0.5% |
| | yeast extract 0.2% |
| | dipottasium phosphate 0.1% |
| | magnesium sulfate heptahydrate 0.05% |

TABLE 4

| No. | MICRO-ORGANISM | No. | ME-DIUM | AMOUNT OF PRODUCTION (NOT ADDED) mg | AMOUNT OF PRODUCTION (ADDED) mg |
|---|---|---|---|---|---|
| 1 | Rhodococcus erythropolis | MAK-34 | 1 | 0.0180 | 1.260 |
| 2 | Mycobacterium chlorophenolicum | IFO-15527 | 3 | 0.0320 | 0.770 |
| 3 | Mycobacterium smegmatis | IAM-12065 | 3 | 0.0480 | 0.210 |
| 4 | Nocardioides simplex | IFO-12069 | 2 | 0 | 0.190 |
| 5 | Klebsiella pneumoniae | IFO-3319 | 2 | 0.0180 | 0.066 |
| 6 | Absidia lichtheimi | IFO-4409 | 4 | 0.0035 | 0.220 |
| 7 | Aspergillus awamori | IFO-4033 | 4 | 0.00048 | 1.170 |
| 8 | Aspergillus candidus | IFO-5468 | 4 | 0.0092 | 0.018 |
| 9 | Penicillium cyaneum | IFO-5337 | 4 | 0.0310 | 1.260 |
| 10 | Hypocrea gelatinosa | IFO-9165 | 4 | 0.0058 | 0.640 |
| 11 | Helicostylum nigricans | IFO-8091 | 4 | 0.0067 | 0.520 |
| 12 | Tritirachium oryzae | IFO-7544 | 4 | 0.0047 | 0.078 |
| 13 | Armillariella mellea | IFO-31616 | 4 | 0.0042 | 0.460 |

Example 6

(Influence of Inducer Addition (2))

Cultures and reactions were carried out as in Example 5 except that microorganisms and media shown in Table 4 were used in place of the microorganism of Example 5. The cells were separated by centrifuge or filtration from culture media (No. 3 and Nos. 6 to 13). As a result, the amount of production of d-pseudoephedrine in the case of the culture with 1-amino-2-hydroxypropane added thereto was remarkably greater than that in the case of culture without addition as shown in Table 4.

Example 7

(Influence of Inducer Addition (3))

Cultures and reactions were carried out as in Example 5 except that 1-amino-2-hydroxypropane in Example 5 was replaced by 1-amino-2-hydroxybutane. The cells were separated by centrifuge or filtration from culture medium. As a result, the amount of production of d-pseudoephedrine in the case of culture with the compound added thereto was remarkably greater than that in the case of culture without addition as shown in Table 5.

TABLE 5

| No. | MICRO-ORGANISM | No. | ME-DIUM | AMOUNT OF PRODUCTION (NOT ADDED) mg | AMOUNT OF PRODUCTION (ADDED) mg |
|---|---|---|---|---|---|
| (14) | Rhodococcus erythropolis | MAK-34 | 1 | 0.0180 | 0.65 |
| (15) | Mycobacterium smegmatis | IAM-12065 | 3 | 0.0480 | 0.17 |

Example 8

(Influence of Inducer Addition (4))

Cultures and reactions were carried out as in Example 5 except that 1-amino-2-hydroxypropane in Example 5 was replaced by 1-amino-2-hydroxycyclohexane. The cells were separated by centrifuge or filtration from culture medium. As a result, the amount of production of d-pseudoephedrine in the case of the culture with the compound added thereto was remarkably greater than that in the case of culture without addition as shown in Table 6.

TABLE 6

| No. | MICRO-ORGANISM | No. | ME-DIUM | AMOUNT OF PRODUCTION (NOT ADDED) mg | AMOUNT OF PRODUCTION (ADDED) mg |
|---|---|---|---|---|---|
| (16) | Rhodococcus erythropolis | MAK-34 | 1 | 0.0180 | 0.23 |
| (17) | Mycobacterium smegmatis | IAM-12065 | 3 | 0.0480 | 0.13 |

Example 9

(Influence of Inducer Addition (5))

Rhodococcus erythropolis MAK-34 strain was planted in 5 ml of a medium at pH 7.0 containing 1.0% of saccharose, 0.5% of corn steep liquor, 0.1% of potassium dihydrogenphosphate, 0.3% of dipotassium hydrogenphosphate, 0.01% of p-aminobenzoic acid, and 0.1% of various kinds of inducers, and was shaking-cultured at 30° C. for 48 hours. The culture medium was centrifuged, so as to yield the cells, which were then put into a test tube, and were suspended with 1.0 ml of 0.2-M sodium phosphate buffer solution (pH 7.0) added thereto. With 10 mg of dl-2-methylaminopropiophenone hydrochloride and 20 mg of glucose added thereto, the suspension was shaken at 30° C. for 16 hours, so as to effect a reaction. After the reaction was completed, the reaction mixture was centrifuged, so as to remove the cells, whereas the supernatant was subjected to HPLC (μBondapakphenyl, manufactured by Waters Corporation, with a diameter of 4 mm, a length of 300 mm, an eluent of 0.05 M sodium phosphate buffer solution (containing 7% of acetonitrile, at pH 6.5), a flow rate of 0.8 mL/min, and a detection wavelength of 220 nm), whereby an optically active pseudoephedrine was obtained. The amount of production thereof was remarkably greater than that in the case with no inducer addition as shown in Table 7.

TABLE 7

| No. | COMPOUND NAME | AMOUNT OF PRODUCTION (mg) |
|---|---|---|
| (18) | 1-acetylamino-2-hydroxypropane | 3.00 |
| (19) | 1-methylamino-2-hydroxypropane | 2.83 |
| (20) | 1-amino-2-oxopropane | 1.97 |
| (21) | 1-amino-2-hydroxycyclopentane | 1.93 |
| (22) | 1-amino-2,3-dihydroxypropane | 1.55 |
| (23) | L-threonine | 1.12 |
| (24) | 4-amino-3-hydroxybutanoic acid | 0.97 |
| (25) | 1-amino-2-oxocyclohexane | 0.26 |
| (26) | Morpholine | 0.11 |
| (27) | 3-hydroxypyrrolidine | 0.11 |
| (28) | 3-hydroxypiperidine | 0.10 |
| (29) | 2-aminomethyltetrahydrofuran | 0.10 |
| (30) | 1-(2-hydroxypropyl)amino-2-hydroxypropane | 0.05 |
| (31) | 1-t-butyloxycarbonylamino-2-hydroxypropane | 0.05 |

TABLE 7-continued

| No. | COMPOUND NAME | AMOUNT OF PRODUCTION (mg) |
|---|---|---|
| (32) | 2-amino-3-hydroxybutane | 0.05 |
| (33) | DL-serine | 0.04 |
|  | no addition | 0.02 |

INDUSTRIAL APPLICABILITY

As explained in the foregoing, the aminoketone asymmetric reductase, protein, nucleic acid, and microorganism of the present invention can provide an aminoketone asymmetric reductase which can act to produce, with a high yield and a high selectivity, a β-aminoalcohol having a desirable optical activity from an enantiomer mixture of an α-aminoketone compound or a salt thereof. Also, a protein having an aminoketone asymmetric reduction activity, a nucleic acid coding the protein, a transformant transformed by the said nucleic acid, a method of producing the protein using the transformant, and uses of the transformant or protein can be provided. Further, a new microorganism which efficiently converts an enantiomer mixture of an α-aminoketone compound or a salt thereof into an optically active β-aminoalcohol can be provided.

The invention claimed is:

1. An isolated protein comprising the amino acid sequence set forth in SEQ ID NO: 1 in the Sequence Listing.

2. An isolated protein encoded by a DNA that hybridizes under highly stringent conditions comprising washing in 6.0×SCC at 65° C. with nucleic acid comprising the nucleotide sequence set forth in SEQ ID NO: 2, wherein said protein has an aminoketone asymmetric reduction activity.

3. A salt of the protein according to claim 1 or 2.

4. An isolated protein obtained by being expressed in a transformant having a vector containing a nucleic acid encoding a protein comprising the amino acid sequence according to claim 1 or 2.

* * * * *

SEQUENCE LISTING

<160> NUMBER OF SEQ ID NOS: 13

<210> SEQ ID NO 1
<211> LENGTH: 259
<212> TYPE: PRT
<213> ORGANISM: Rhodococcus erythropolis

<400> SEQUENCE: 1

```
Met Phe Asn Ser Ile Glu Gly Arg Ser Val Val Val Thr Gly Gly Ser
1               5                   10                  15

Lys Gly Ile Gly Leu Gly Met Val Arg Val Phe Ala Arg Ala Gly Ala
            20                  25                  30

Asn Val Leu Met Thr Ala Arg Asp Ala Leu Thr Leu Glu Arg Ala Ala
        35                  40                  45

Glu Gly Leu Asn Gly Leu Pro Gly Ala Val Ser Thr Leu Gln Val Asp
    50                  55                  60

Val Thr Asn Pro Asp Ser Leu Ala Gly Met Ala Glu Val Ala Ala Glu
65                  70                  75                  80

Arg His Gly Gly Ile Asp Val Leu Cys Ala Asn Ala Gly Ile Phe Pro
                85                  90                  95

Ser Lys Arg Leu Gly Glu Met Thr Ser Glu Asp Met Asp Ser Val Phe
            100                 105                 110

Gly Val Asn Val Lys Gly Thr Ile His Ala Val Gln Ala Cys Met Pro
        115                 120                 125

Trp Leu Glu Thr Ser Gly Arg Gly Arg Val Val Val Thr Ser Ser Ile
    130                 135                 140

Thr Gly Pro Val Thr Gly Tyr Pro Gly Trp Ser His Tyr Gly Ala Ser
145                 150                 155                 160

Lys Ala Ala Gln Met Gly Phe Ile Arg Thr Ala Ala Ile Glu Leu Ala
                165                 170                 175
```

```
Pro Lys Arg Ile Thr Ile Asn Ala Val Leu Pro Gly Asn Val Ile Thr
            180                 185                 190

Glu Gly Leu Asp Gly Leu Gly Gln Glu Tyr Leu Asp Gln Met Ala Ser
        195                 200                 205

Ser Val Pro Ala Gly Ser Leu Gly Ser Val Glu Asp Ile Ala Asn Ala
    210                 215                 220

Ala Leu Phe Phe Ala Leu Asp Glu Ala Ala Tyr Ile Thr Gly Gln Ser
225                 230                 235                 240

Leu Ile Val Asp Gly Gln Val Leu Pro Glu Ser Ala Met Ala Leu
                245                 250                 255

Gly Glu Leu

<210> SEQ ID NO 2
<211> LENGTH: 780
<212> TYPE: DNA
<213> ORGANISM: Rhodococcus erythropolis

<400> SEQUENCE: 2
atgttcaact ccattgaagg tcgttcggtc gtcgtcaccg gcggtagcaa gggcatcggc      60
ttgggaatgg tccgggtatt cgcgcgcgca ggggccaatg tgctcatgac cgcgcgagac     120
gctctgactc tcgaacgtgc cgcggagggt ttgaatggtc ttcctggcgc ggtctccaca     180
cttcaagtcg acgtcacgaa tcctgactcc ttggccggta tggcagaagt tgcggccgag     240
cgacacggag gaatcgacgt gttgtgcgcg aacgctggga tcttcccgtc gaagcggttg     300
ggagagatga cctcggagga catggacagc gtattcggcg tcaacgtcaa ggggaccatc     360
cacgccgtgc aagcgtgcat gccgtggctc gaaacttctg ggcgtggaag ggttgtcgtg     420
acatcgtcga tcaccggacc cgtaaccggt tatccgggtt ggtcgcacta cggggcaagc     480
aaggctgcgc agatgggctt catccgaact gctgccattg agttggcacc gaagaggatc     540
acgatcaacg ccgtcttgcc cggcaacgtg atcaccgagg ggctcgacgg tttgggacag     600
gaatatctcg accaaatggc gtccagcgtc ccggccggca gtctgggcag cgtcgaggat     660
atcgccaatg ccgcactgtt ctttgcactg gacgaagccg cgtacatcac cggtcagtcg     720
ttgatcgtag atggtggaca ggttcttccg gagtcggcga tggcgctcgg cgaactgtaa     780

<210> SEQ ID NO 3
<211> LENGTH: 17
<212> TYPE: PRT
<213> ORGANISM: Rhodococcus erythropolis

<400> SEQUENCE: 3

Met Phe Asn Ser Ile Glu Gly Arg Ser Val Val Val Thr Gly Gly Ser
1               5                   10                  15

Lys

<210> SEQ ID NO 4
<211> LENGTH: 19
<212> TYPE: PRT
<213> ORGANISM: Rhodococcus erythropolis

<400> SEQUENCE: 4

Arg Leu Gly Glu Met Thr Ser Glu Asp Met Asp Ser Val Phe Gly Val
1               5                   10                  15

Asn Val Lys
```

```
<210> SEQ ID NO 5
<211> LENGTH: 17
<212> TYPE: PRT
<213> ORGANISM: Rhodococcus erythropolis

<400> SEQUENCE: 5

Ala Ala Gln Met Gly Phe Ile Arg Thr Ala Ala Ile Glu Leu Ala Pro
1               5                   10                  15

Lys

<210> SEQ ID NO 6
<211> LENGTH: 13
<212> TYPE: PRT
<213> ORGANISM: Rhodococcus erythropolis
<220> FEATURE:
<221> NAME/KEY: UNSURE
<222> LOCATION: (1)..(2)
<223> OTHER INFORMATION: Xaa is unidentified from peptide sequencing
<220> FEATURE:
<221> NAME/KEY: UNSURE
<222> LOCATION: (12)..(12)
<223> OTHER INFORMATION: Xaa is unidentified from peptide sequencing

<400> SEQUENCE: 6

Xaa Xaa Ile Leu Ala Val Gln Ala Met Met Pro Xaa Leu
1               5                   10

<210> SEQ ID NO 7
<211> LENGTH: 28
<212> TYPE: PRT
<213> ORGANISM: Rhodococcus erythropolis
<220> FEATURE:
<221> NAME/KEY: UNSURE
<222> LOCATION: (1)..(1)
<223> OTHER INFORMATION: Unidentified from peptide sequencing
<220> FEATURE:
<221> NAME/KEY: UNSURE
<222> LOCATION: (1)..(1)
<223> OTHER INFORMATION: Xaa is unidentified from peptide sequencing

<400> SEQUENCE: 7

Xaa Ile Thr Ile Asn Ala Val Leu Pro Gly Asn Val Ile Thr Glu Gly
1               5                   10                  15

Leu Asp Gly Leu Gly Gln Glu Tyr Leu Asp Gln Met
            20                  25

<210> SEQ ID NO 8
<211> LENGTH: 23
<212> TYPE: DNA
<213> ORGANISM: Artificial Sequence
<220> FEATURE:
<223> OTHER INFORMATION: Oligo Primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 8
atgttyaayw snathgargg nmg                                          23

<210> SEQ ID NO 9
<211> LENGTH: 26
<212> TYPE: DNA
<213> ORGANISM: Artificial Sequence
<220> FEATURE:
```

```
-continued

<223> OTHER INFORMATION: Oligo Primer
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 9
catytgrtcn arrtaytcyt gnccna                                       26

<210> SEQ ID NO 10
<211> LENGTH: 26
<212> TYPE: DNA
<213> ORGANISM: Artificial Sequence
<220> FEATURE:
<223> OTHER INFORMATION: Oligo Primer

<400> SEQUENCE: 10
aatacccgga ccattcccaa gccgat                                       26

<210> SEQ ID NO 11
<211> LENGTH: 26
<212> TYPE: DNA
<213> ORGANISM: Artificial Sequence
<220> FEATURE:
<223> OTHER INFORMATION: Oligo Primer

<400> SEQUENCE: 11
tcgaaacttc tgggcgtgga agggtt                                       26

<210> SEQ ID NO 12
<211> LENGTH: 29
<212> TYPE: DNA
<213> ORGANISM: Artificial Sequence
<220> FEATURE:
<223> OTHER INFORMATION: Oligo Primer

<400> SEQUENCE: 12
gatgaattcc aaatgttcaa ctccattga                                    29

<210> SEQ ID NO 13
<211> LENGTH: 29
<212> TYPE: DNA
<213> ORGANISM: Artificial Sequence
<220> FEATURE:
<223> OTHER INFORMATION: Oligo Primer

<400> SEQUENCE: 13
tgaagctttc gtcgcttgtc ttacagttc                                    29
```